United States Patent
Gustafson et al.

(10) Patent No.: US 6,733,057 B2
(45) Date of Patent: May 11, 2004

(54) APPARATUS FOR BREAKING OFF CORES

(76) Inventors: Dovovan Lee Gustafson, 6719 S. Lien Rd., South Range, WI (US) 54874; Theodore Allen Spencer, 5937 Arnold Rd., Duluth, MN (US) 55803

( * ) Notice: Subject to any disclaimer, the term of this patent is extended or adjusted under 35 U.S.C. 154(b) by 0 days.

(21) Appl. No.: 09/683,938

(22) Filed: Mar. 5, 2002

(65) Prior Publication Data

US 2003/0168870 A1 Sep. 11, 2003

(51) Int. Cl.[7] ............................................... A01D 11/00
(52) U.S. Cl. .................... 294/50.7; 294/50.6; 294/50.8; 172/371; 172/381
(58) Field of Search .............................. 294/50.6, 50.7, 294/50.8; 172/371, 381; 73/864.44; 175/20, 244, 249, 403

(56) References Cited

U.S. PATENT DOCUMENTS

| | | | |
|---|---|---|---|
| 4,974,682 A | * | 12/1990 | Hoffman ...................... 172/22 |
| 5,328,221 A | * | 7/1994 | Richardson, Jr. .......... 294/50.7 |
| 5,431,466 A | * | 7/1995 | Richardson, Jr. .......... 294/50.7 |
| 5,445,229 A | * | 8/1995 | Delima ........................ 175/20 |

* cited by examiner

Primary Examiner—Eileen D. Lillis
Assistant Examiner—Michael S Lowe
(74) Attorney, Agent, or Firm—Rudy Law Firm; William T. Helwig

(57) ABSTRACT

An Apparatus and method for breaking off cores from a material to be tested includes a tube split by opposing slots, a tightening device for moving confronting ends of a split tube towards each other so that the split tube grasps the core to be broken, and a handle for exerting lateral forces to break off the core. The core breaker is inserted into a space left by a core drill bit. The split tube is tightened around the core to be broken off, and lateral pressure is then applied to the handle to break off the core.

3 Claims, 5 Drawing Sheets

APPARATUS FOR BREAKING OFF CORES

BACKGROUND OF INVENTION

The present invention relates in general to an apparatus and method for obtaining test core samples and in particular to an apparatus and method for obtaining test core samples from pavement.

In the paving industry, State Dept. of Transportation, County, City and Federal Aviation Administration Officials, Authorities and Engineers as well as the above from the private sector of the construction industry, require that paving contractors of their representatives drill out core samples of the pavement within certain time constraints, or at a later time for investigative and informational purposes. These cores are subjected to various tests to verify different properties and density. The core samples are generally obtained by using a vertical core drill which drills out a core of the pavement using a tubular diamond-tipped bit driven by a gas or electric drilling machine. The cores will generally vary in length and are of varying diameters, depending on the agency specifications and/or preference of the testers.

To test the cores and obtain results that are representative in general, it is important to obtain the cores in a timely and cost effective manner. Several methods presently used to obtain core samples are: 1) Drilling a second identical core next to the sample core hole, chipping out the second core hole and then getting under the sample core with a lever and prying it out. 2) Driving a pair of rods through the surrounding material and prying out the core. 3) Digging a wedge shaped hole next to the core and prying it out. 4) Drilling through the entire depth of the pavement and extracting the core from the hole using an apparatus for pulling cores such as that described in the Richardson, Jr. Patent (U.S. Pat. No. 5,431,466), which represents the present state of the art. These methods are time consuming, hence labor costly and materials (core bit) costly, due to having to drill (in many instances) the depth of the full pavement, when only a small portion of the top surface may be tested.

With the specifying agencies continuously requiring a better product and more quality control, the number of cores to be drilled and tested has increased. The problem of obtaining test cores in a timely and cost effective manner has increased over the past years. This is particularly true where the pavement to be tested is a surface layer of asphalt (2 inches is common) underlaid with 8 inches of concrete (common on large expressways). Drilling a core through the full depth of pavement under these circumstances can take 45 minutes or longer and may wear out a single 4 inch diamond tipped core bit at an average cost of $300 or more. This is an extremely inefficient use of time and materials when it is common that only the top 2 inches of asphalt is required for examination. This top layer of asphalt can be drilled in substantially less time than drilling the full depth of pavement (approximately 2 minutes or less), especially when drilling a full core requires drilling through concrete. Drilling only the top layer also saves dramatically on equipment, where a single core bit may last through several hundred cores of the top layer of asphalt. What is needed is a tool that can efficiently and easily break off and extract cores from pavement surfaces without the necessity of drilling the depth of full pavement.

SUMMARY OF INVENTION

It is an object of the present invention to provide an apparatus and method for obtaining undamaged test cores which only requires drilling to a specified depth in the top surface, and does not require drilling the full depth of pavement.

It is another object of the invention to provide an apparatus and method for obtaining test cores in a timely and cost effective manner.

It is a further object of invention to provide an apparatus and method of obtaining test cores which can be used with industry standard drill bits for taking core samples from the pavement.

These and other objects and advantages of the present invention are realized in one embodiment of an apparatus for breaking off cores, comprising a split tube, a handle attached to the top of the split tube, and tightening device for moving confronting ends of the split tube towards each other and away from each other if desired, the tightening device being located on the middle portion of the split tube.

The method of the present invention includes the steps of providing an apparatus for the breaking off of cores, inserting the apparatus to a predetermined depth in a space that has been drilled around a core with industry standard drill bits, tightening the apparatus and using lateral force to break off the core.

BRIEF DESCRIPTION OF DRAWINGS

The present invention may be understood from the description of the embodiment which follows and from the accompanying drawings. The drawings are hereby expressly made a part of the specification.

DETAILED DESCRIPTION

Figure 1:
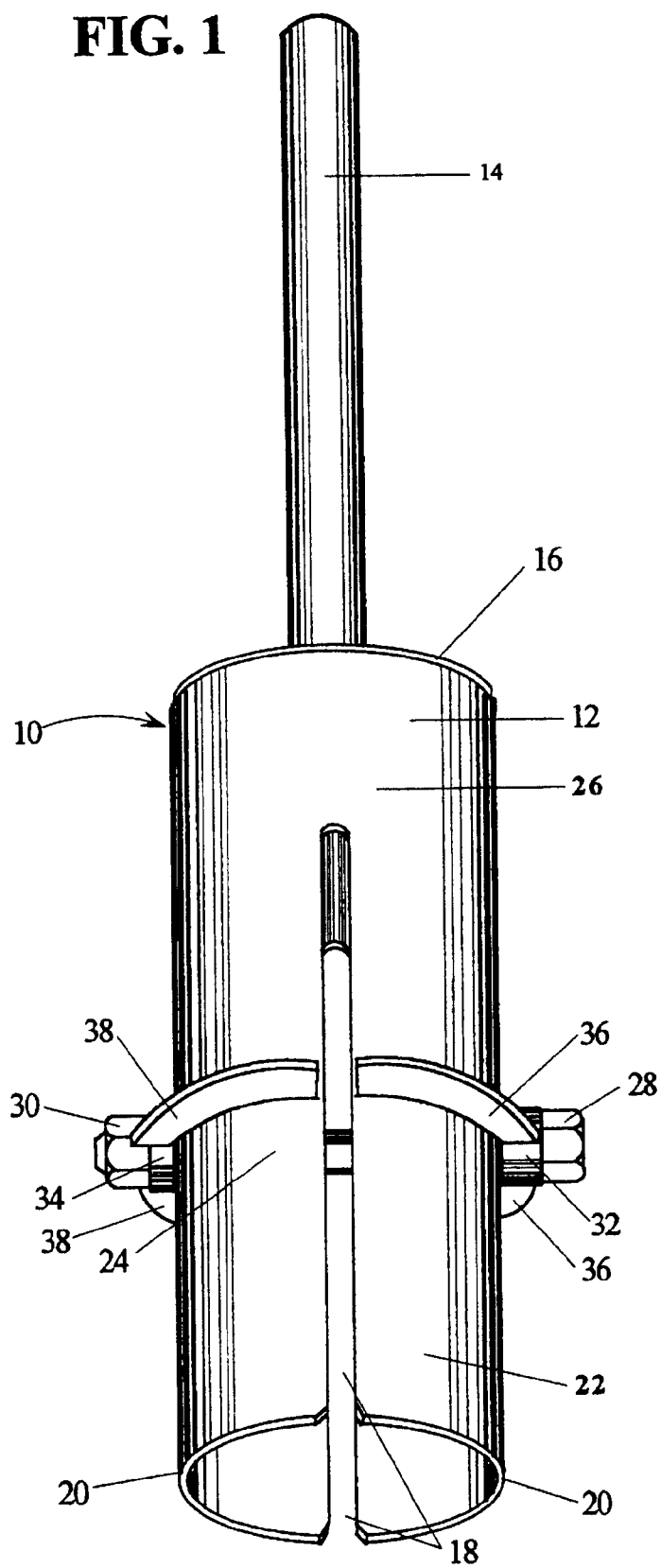
FIG. 1—is a perspective view of the embodiment of the invention.
Figure 2:
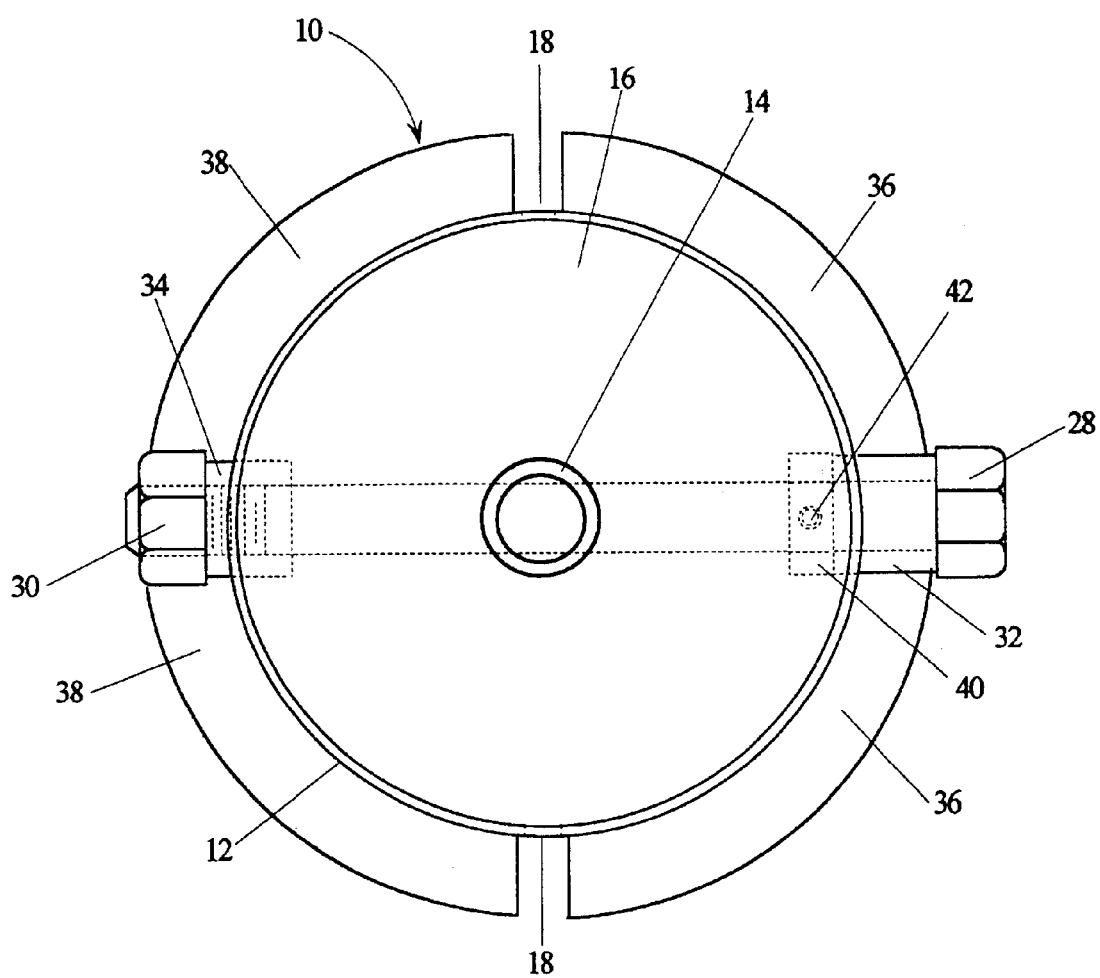
FIG. 2—is a top view of the embodiment of the invention.
Figure 3:
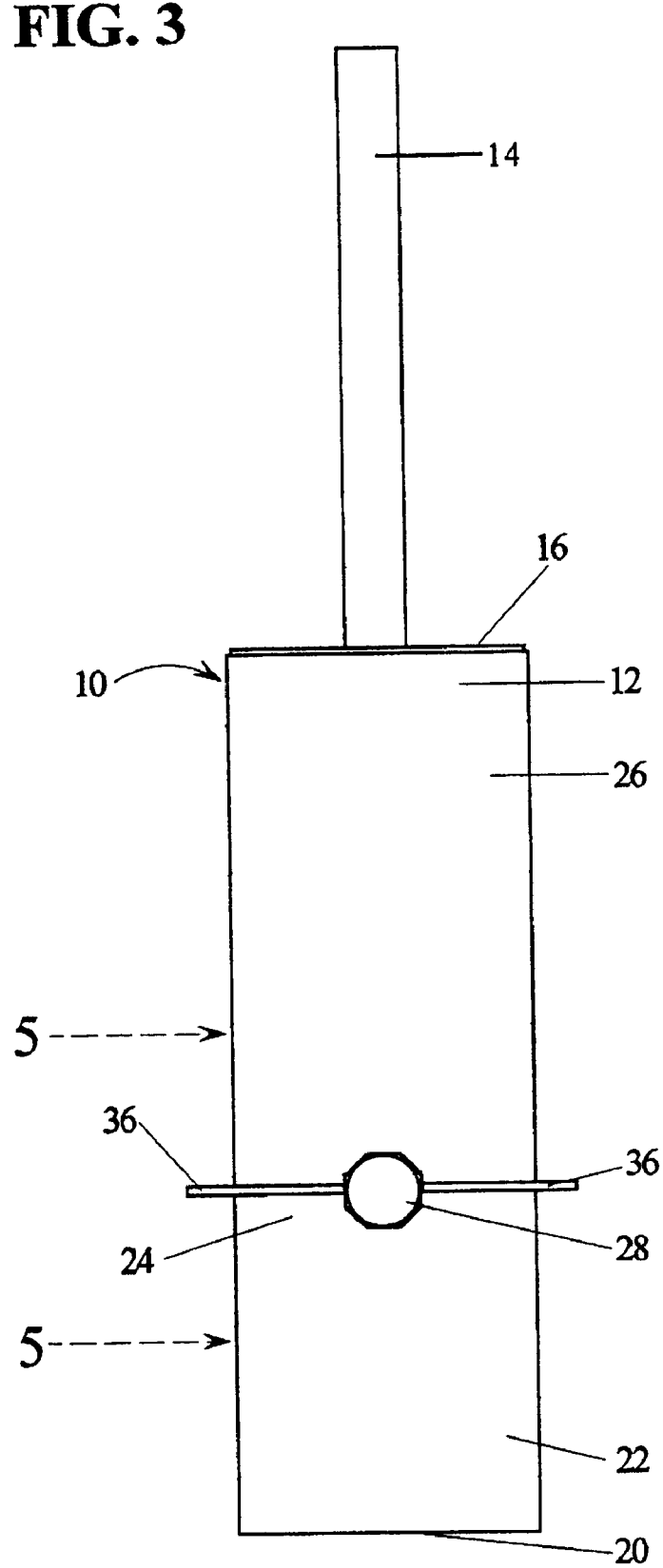
FIG. 3—is a front view of the embodiment of the invention.
Figure 4:
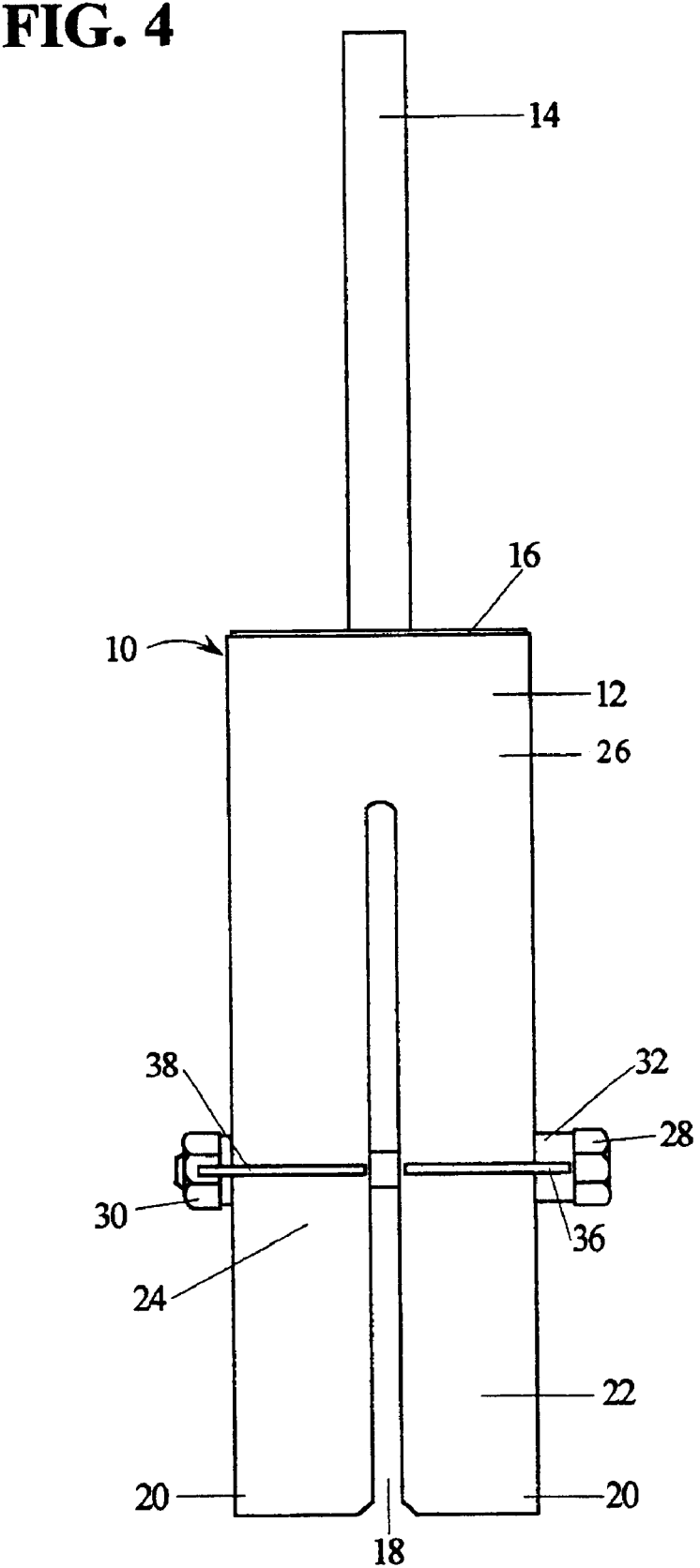
FIG. 4—is a side view of the embodiment of the invention.

Referring first to FIG. 1, the embodiment (10) of the slotted (18) cylindrical split tube (12) having two opposing slots (18), a top plate (16) and a handle (14). A tightening device for moving confronting ends (20) of the split tube (12) towards each other includes strengthening gussets (36), (38), clamping bolt (28), nut (30), bushings (32), (34), and (FIG. 5) collar (40) and roll pin (42).

The split tube (12) has a lower area (22) mid-area (24) and upper area (26). The gussets (36), (38), clamping bolt (28), nut (30), bushings (32), (34), collar (40) and roll pin (42) are mounted in the mid-area (24) so that the lower area (22) is free from external obstructions, thereby allowing insertion of the lower area (22) into the cylindrical space created by the core drill bit used. One standard drill bit used in the industry is approximately four inches in diameter, therefore, a diameter of the split tube (12) may be approximately four inches, but other diameters are common.

Slots (18) are cut from the bottom edge of the lower area (22) into the upper area (26) of sufficient height and width to allow the split tube (12) to undergo elastic deformation when the clamping bolt (28) is tightened and loosened.

The length of the unobstructed lower area (22) is varied according to the depth of the core to be broken off.

Generally, the length of the lower area (22) is approximately six and one-half inches, but other lengths are possible. The thickness of the split tube (12) must be slightly less than the thickness of the standard core drill bit being used. The handle (14) may be made from ¾" diameter pipe and is welded to the center area of the top plate (16), which is welded to the top of the split tube (12). The handle (14) should be of sufficient length to provide the necessary lateral leverage for the breaking off of a core. The top plate (16) may be made from three sixteenths inch thick plate steel.

The split tube (12) has holes for receiving the bushings (32), (34). The clamping bolt (28) is inserted through the bushings (32), (34). The clamping bolt (28) and nut (30) arrangement can be any of those known in the art whereby the clamping bolt (28) is rotated into the nut (30) and the confronting ends (20) of the split tube (12) are forced towards each other.

Figure 5:
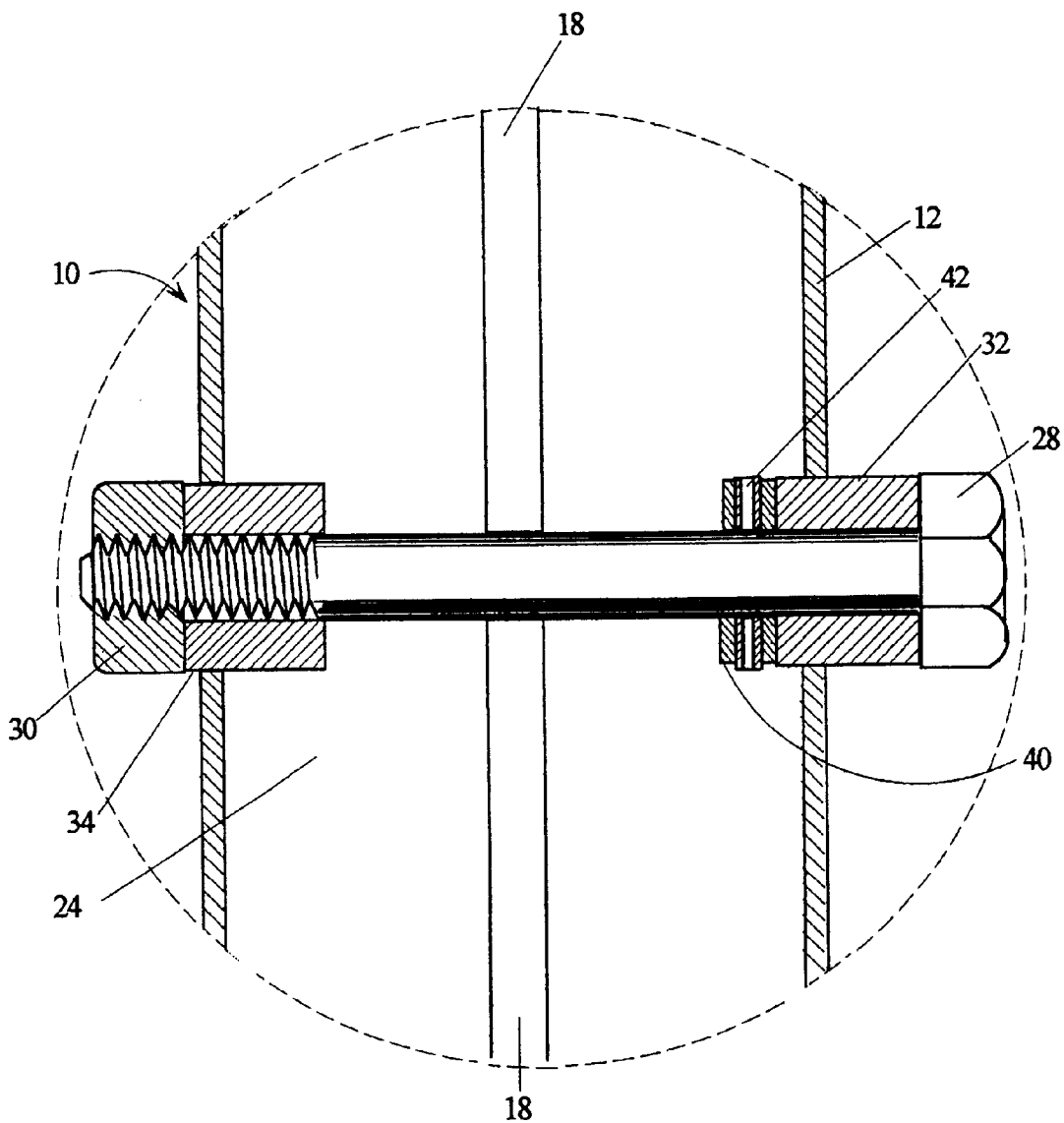
FIG. 5—is an enlarged cross-sectional side view of FIG. 3 as indicated by line 5—5, and a direct cross-sectional enlarged view of FIG. 4.

The arrangement of FIG. 5 includes bushings (32), (34) welded to the mid-area (24) of the split tube (12). The nut (30) is welded to bushing (34). The clamping bolt (28) is inserted through bushing (32). Clamping bolt (28) passes through busing (32) collar (40) bushing (34) and threaded into nut (30). Collar (40) may be pinned or welded to the clamping bolt (28) (roll pin depicted). The function of the collar (40) and roll pin (42) is to act as a stop, when the clamping bolt (28) is loosened, to allow the confronting ends (20) of the split tube (12) to separate, to release the core that has been broken off.

Strengthening gussets (36) are welded to the split tube (12) and bushing (32). Gussets (38) are welded to the split tube (12) bushing (34) and nut (30). The gussets (36), (38) may be made of three sixteenths inch thick plate steel. The clamping bolt (28) may be a ¾" bolt, 7" long with a threaded end. A standard device such as a ratchet and socket the same size as the nut (30) may be used to tighten and loosen the clamping bolt (28).

The preferred method for breaking off a core from a material to be tested includes: providing the preferred embodiment of an apparatus (10) for breaking off cores, inserting the lower portion of the split tube (22) into a space left by a core drill bit, tightening the clamping bolt (28) so that the split tube (12) is tightened around the core to be broken off, grasping the core securely with the confronting ends (20) of the split tube (12) so as to prevent the fracturing or shearing off of the core during the application of breaking forces except at the desired depth, applying a lateral force to the handle (14) attached to the top plate (16) of the split tube (12) sufficient to break off the core, transmitting the applied force through the split tube (12) to the base of the split tube (12) where the confronting ends (20) of the split tube (12) are grasping the core at the desired depth, breaking off the core at the desired depth in an otherwise undamaged state, lifting the core out of the hole by the handle (14), loosening the clamping bolt (28) so that the split tube (12) is opened around the core, and releasing the core so that it may be removed from the apparatus. The method and embodiment of the present invention shown and discussed are by way of illustration and not of limitation, and a wide variety of equivalent methods and embodiments may be made without departing from the spirit or scope of the invention.

What is claimed is:

1. An apparatus for breaking off a partially drilled core surrounded by a space, comprising:

a grasping means by which a partially drilled core may be securely grasped so as to prevent the fracturing or shearing off of said core during the application of breaking forces except at the desired depth; and, a lever means attached to the top of said grasping means by which a lateral force is applied to the distal end of said lever means and which force is then transmitted through said grasping means to a point of application of said force sufficient to break off said core at the desired depth.

2. A method for breaking off a core surrounded by a space, comprising:

grasping a core securely so as to prevent the fracturing or shearing off of said core during the application of breaking forces except at the desired depth using a grasping means;

applying a lateral force to a lever means attached to said grasping means and transmitting said force through said grasping means to a point of application of said force sufficient to break off said core at the desired depth; and, breaking off said core at the desired depth in an otherwise undamaged state.

3. An apparatus for breaking off a core surrounded by a space, comprising:

a handle and a tool element extending from said handle including a top surface to which the handle is centrally attached;

a cylindrical tube extending downward from said top surface which is split longitudinally by opposing slots extending from the base of the tube upwards for more than half of said tubes length;

a tightening device for moving the confronting ends of the split tube towards each other, the tightening device being located in the middle portion of said split tube; wherein the lower portion of said tube is sized to fit in the space surrounding a core and of a length to extend into said space to a specified depth; and wherein said slots in the tube allow for elastic deformation of the lower half of the tube when acted upon by said tightening device for the grasping and release of cores; and wherein said split tube when tightened grasps the core securely so as to prevent the fracturing or shearing off of said core during the application of breaking forces except at the desired depth which is at said confronting ends at the base of said split tube; and wherein said handle is of sufficient length and material that a lateral force applied to the distal end of said handle and transmitted through the split tube to the point of application of force at the base of said split tube will cause a core to break off at the desired depth.

* * * * *

UNITED STATES PATENT AND TRADEMARK OFFICE
CERTIFICATE OF CORRECTION

PATENT NO. : 6,733,057 B2
DATED : May 11, 2004
INVENTOR(S) : Theodore Allen Spencer and Donovan Lee Gustafson It is certified that error appears in the above-identified patent and that said Letters Patent is hereby corrected as shown below:

Title page,
Item [12], United States Patent, "Gustafson et al." should read -- Spencer et al. --
Item [76], Inventors, "Donovan Lee Gustafson, 6719 S. Lien Rd., South Range, WI (US) 54874; Theodore Allen Spencer, 5937 Arnold Rd., Duluth, MN (US) 55803" should read -- Theodore Allen Spencer, 5937 Arnold Rd., Duluth, MN (US) 55803; Donovan Lee Gustafson, 6719 S. Lien Rd., South Range, WI (US) 54874 --

Signed and Sealed this

Tenth Day of August, 2004

JON W. DUDAS
*Acting Director of the United States Patent and Trademark Office*